(12) United States Patent
Maunoury et al.

(10) Patent No.: US 10,644,243 B2
(45) Date of Patent: May 5, 2020

(54) N-PHENYL TRISCARBAZOLE

(75) Inventors: Jonathan Maunoury, Brussels (BE); Enrico Orselli, Brussels (BE); Alexandre Ferrand, Brussels (BE); Dominique Bascour, Grez-Doiceau (BE)

(73) Assignee: Nissan Chemical Industries, Ltd., Tokyo (JP)

( * ) Notice: Subject to any disclaimer, the term of this patent is extended or adjusted under 35 U.S.C. 154(b) by 928 days.

(21) Appl. No.: 13/818,292

(22) PCT Filed: Aug. 23, 2011

(86) PCT No.: PCT/EP2011/064426
§ 371 (c)(1),
(2), (4) Date: Sep. 11, 2013

(87) PCT Pub. No.: WO2012/025510
PCT Pub. Date: Mar. 1, 2012

(65) Prior Publication Data
US 2014/0001449 A1    Jan. 2, 2014

Related U.S. Application Data

(60) Provisional application No. 61/406,888, filed on Oct. 26, 2010.

(30) Foreign Application Priority Data

Aug. 26, 2010  (EP) ..................................... 10174232
Oct. 11, 2010  (EP) ..................................... 10187155

(51) Int. Cl.
*H01L 51/00* (2006.01)
*C09K 11/06* (2006.01)
(Continued)

(52) U.S. Cl.
CPC ........ *H01L 51/0056* (2013.01); *C07D 209/88* (2013.01); *C09K 11/06* (2013.01);
(Continued)

(58) Field of Classification Search
CPC combination set(s) only.
See application file for complete search history.

(56) References Cited

U.S. PATENT DOCUMENTS

2003/0205696 A1* 11/2003 Thoms ................... C09K 11/06
                                                            252/301.16
2005/0158578 A1*  7/2005 Iwakuma ............... C09K 11/06
                                                            428/690
(Continued)

FOREIGN PATENT DOCUMENTS

CN        1702066        11/2005
EP     2 096 690 A2       9/2009
(Continued)

OTHER PUBLICATIONS

Tsai et al. ("3-(9-carbazolyl)carbazoles and 3,6-di(9-carbazolyl)carbazoles as effective host materials for efficient blue organic electrophosphorescence") (2007).*
Tsai et al. "2-(9-Carbazolyl)carbazoles and 3,9-Di(9-carbazolyl)carbazoles as Effective Host Materials for Efficient Blue Organic Electrophosphorescence" (2007).*
Q. Zhang et al.: "Carbazole-based hole-transporting materials for electroluminiscence devices", Synthetic Metals, vol. 137, 2003, pp. 1111-1112.
T. Xu et al.: "Phosphorous(V) porphyrins with axial carbazole-based dendritic substituents", Organic Letters, vol. 9, No. 5, Jan. 2, 2007 (Jan. 2, 2007), pp. 797-800.

(Continued)

*Primary Examiner* — Austin Murata
(74) *Attorney, Agent, or Firm* — The Marbury Law Group, PLLC

(57) ABSTRACT

The present invention relates to a novel triscarbazole compound having substituent on N-phenyl, which can be represented by Formula (I). wherein $R_1$ is selected from the group consisting of hydrogen, halogen or alkyl or alkoxy group having 1 to 20 carbon atoms wherein at least one hydrogen atom is optionally replaced by halogen; $R_A$, $R_B$, $R_C$, $R_D$ and $R_E$ are any of substituents other than hydrogen wherein at least two of $R_1$ and $R_A$ may further form a fused ring; and i, j, k, l and m are same or different at each occurrence and represent an integer from 0 to 4, with the proviso that when $R_1$ is hydrogen, i is not 0. By introduction of the substituent on N-phenyl, the device efficiency, stability and lifetime can be increased while maintaining the solubility. These compounds can be used in various organic devices such as organic light emitting diodes, photovoltaic cells or organic semiconductor devices.

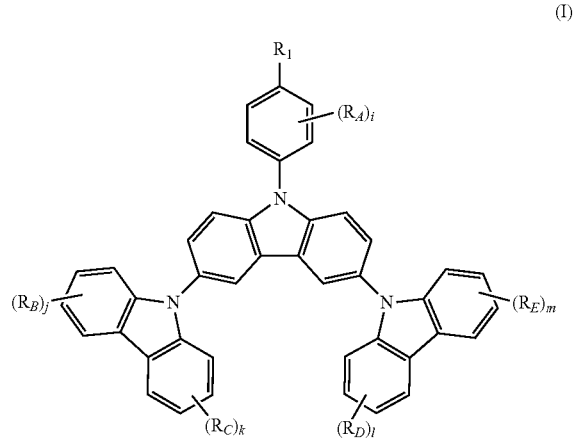

8 Claims, 2 Drawing Sheets

(51) Int. Cl.
  *C07D 209/88* (2006.01)
  *H05B 33/14* (2006.01)
(52) U.S. Cl.
  CPC ...... *H01L 51/0067* (2013.01); *H01L 51/0072* (2013.01); *H05B 33/14* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/18* (2013.01)

(56) References Cited

U.S. PATENT DOCUMENTS

| 2009/0001874 | A1* | 1/2009 | Yen | C07C 211/61 |
| | | | | 313/504 |
| 2010/0141126 | A1 | 6/2010 | Otsu et al. | |
| 2010/0308311 | A1* | 12/2010 | Mitsui | B82Y 10/00 |
| | | | | 257/40 |
| 2012/0172556 | A1* | 7/2012 | Zhang | C07D 413/10 |
| | | | | 526/259 |

FOREIGN PATENT DOCUMENTS

| JP | 2009-021335 A | 1/2009 |
| JP | 2009-021335 A | 1/2009 |
| WO | WO-2004/101517 | 11/2004 |
| WO | 2006096399 | 9/2006 |
| WO | WO-2009/060757 A1 | 5/2009 |
| WO | WO-2009/104488 A1 | 8/2009 |
| WO | 2010043693 | 4/2010 |

OTHER PUBLICATIONS

Tsai et al., "3-(9-Carbazolyl)carbazoles and 3,6-Di(9-carbazolyl)carbazoles as Effective Host Materials for Efficient Blue Organic Electrophosphorescence", Advanced Materials, (2007), 19, pp. 862-866.
Tsai et al., "P-152: Efficient blue phosphorescent OLEDs employing novel oligocarbazoles as high-triplet-energy host materials", Digest of Technical Papers—Society for Information Display International Symposium (2007), 38 (Bk. 1), pp. 772-775.
Zhang et al., "Carbazole-based hole-transporting materials for electroluminescent devices", Synthetic Metals, (2003), 137, pp. 1111-1112.
Baranoff et al., "Cyclometallated iridium complexes for conversion of light into electricity and electricity into light", J. Organomet. Chem. (2009), 694, pp. 2661-2670.
Y. Chi et al., Transition-metal phosphors with cyclometalating ligands: fundamentals and applications, Chem. Soc. Rev., (2010), 39, pp. 638-655.

* cited by examiner

N-PHENYL TRISCARBAZOLE

CROSS REFERENCE TO RELATED APPLICATIONS

This application is the National Phase of International Application No. PCT/EP2011/064426, filed Aug. 23, 2011 which claims priority to U.S. provisional application No. 61/406,888 filed on Oct. 26, 2010, to European application No. 10174232.8 filed on Aug. 26, 2010, and to European application No. 10187155.6 filed on Oct. 11, 2010, the whole content of each of these applications being incorporated herein by reference for all purposes.

TECHNICAL FIELD

The present invention relates to a novel N-phenyl triscarbazole compound having substituent on N-phenyl, and an organic device comprising the compound according to the present invention as well as a light emitting compound.

BACKGROUND ART

Various devices have been under active study and development, particularly those based on electroluminescence (EL) from organic materials. The use of phosphorescent materials has been a major breakthrough in boosting electroluminescence efficiency since they allow simultaneous harvesting of both singlet and triplet excitons.

Unfortunately, the emission lifetimes of these phosphorescent complexes are relatively long, leading to undesired triplet-triplet annihilation during the operation of a device. To overcome this problem, phosphorescent emitters are doped into organic host materials.

Selecting a suitable host material for the phosphorescent dopants remains one of the critical issues in phosphorescence-based organic light emitting diodes (OLED). An ideal host material would meet the following intrinsic requirements: a triplet energy gap (Et) larger than that of the triplet dopant to prevent reverse energy transfer from the guest back to the host, good carrier transporting properties to balance the charge flux and reduce the driving voltage, thermal and morphological stability to extend the device operational lifetime.

Well-known host materials for guest-host systems include hole-transporting 4,4'-N,N'-dicarbazolyl-biphenyl (CBP) and electron-transporting aluminium 8-hydroxyquinoline ($Alq_3$), which have been used in OLED. Those host materials have suitable properties for green and red emitters.

In contrast, highly efficient blue-light emitting phosphorescent devices remain rare, mainly because of the lack of suitable host materials possessing both charge transporting characteristics and high triplet energy.

Several host materials for better phosphorescent emission have been reported. Due to their charge conducting ability, photophysical and redox properties, sufficiently large triplet energies and carrier-transport properties, carbazole-based compounds have been actively studied. Carbazole-based materials simultaneously possess sufficiently large triplet energies and carrier-transport properties.

For carbazole-based molecules to acquire enough morphological stability when they are deposited as thin films, extension of molecular dimensions beyond single carbazole units to obtain sterically bulky molecular configurations is necessary. Some papers, e.g., Adv. Mater. 2007, 19, 862-866 and Synth. Mater. 2007, 157, 529-533 describe that linking carbazole units together to form polycarbazoles or adding substituents on triscarbazole compound can affect the uniformity and stability of an evaporated film.

For example, U.S. Patent Application Publication No. US 2003/205696 discloses guest-host emissive systems suitable for use in OLED in which the host material comprises a compound having a carbazole core with an electron-donating species bonded to nitrogen, aromatic amine groups or carbazole groups bonded to one or more of the carbon atoms, a large band gap potential, and high-energy triplet excited states. Such materials permit short-wavelength phosphorescent emission by an associated guest material, and the combination of said materials with emissive phosphorescent organometallic compounds such as iridium complexes is useful in the fabrication of OLED.

Japan Patent Application Publication No. JP 2009/021335 and International Application No. WO 2009/060757. and WO 2009/060780, and U.S. Patent Application Publication No. US2009/0218938 discloses OLED comprising phenyl triscarbazoles and Ir complexes.

However, none of the above-disclosed materials meets all the requirements necessary for OLED application, particularly suitable energy level, charge transport ability, processability from a solution with uniform film formation, ability to form an amorphous phase, as well as long lifetime under operational conditions of the device. Thus, there has been a need to develop new host materials, which are capable of satisfying all of the requirements indicated above.

SUMMARY OF INVENTION

Surprisingly, it has been found that when substituted phenyl group is introduced to the triscarbazole compound, the OLED efficiency and lifetime are increased compared to those of device comprising triscarbazole compound having unsubstituted phenyl group, without any adverse effects on the other properties such as solubility.

The present invention provides a triscarbazole compound having substituted phenyl group. Specifically, this triscarbazole compound can be represented by Formula (I):

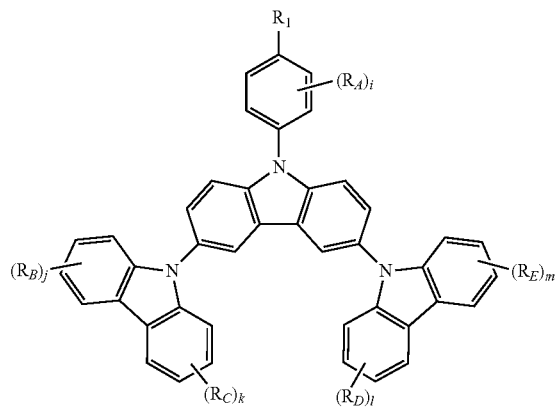

Formula (I)

wherein;
$R_1$ is selected from the group consisting of:
hydrogen;
halogen; and
alkyl or alkoxy group having 1 to 20 carbon atoms wherein at least one hydrogen atom is optionally replaced by halogen;

$R_A$, $R_B$, $R_C$, $R_D$ and $R_E$ are any of substituents other than hydrogen wherein at least two of $R_1$ and $R_A$ may further form a fused ring, and;

i, j, k, l and m are same or different at each occurrence and represent an integer from 0 to 4, with the proviso that when $R_1$ is hydrogen, i is not 0.

The triscarbazole compound of the present invention can be used in various applications, including in OLED, photovoltaic cells or organic semiconductor devices. For example, those compounds can act as an efficient host material for phosphorescent emitters in OLED.

The present invention also provides a device, preferably a light emitting device, comprising having the N-phenyl triscarbazole compound as well as Ir complex.

DESCRIPTION OF EMBODIMENTS

Figures 1, 2, 3:
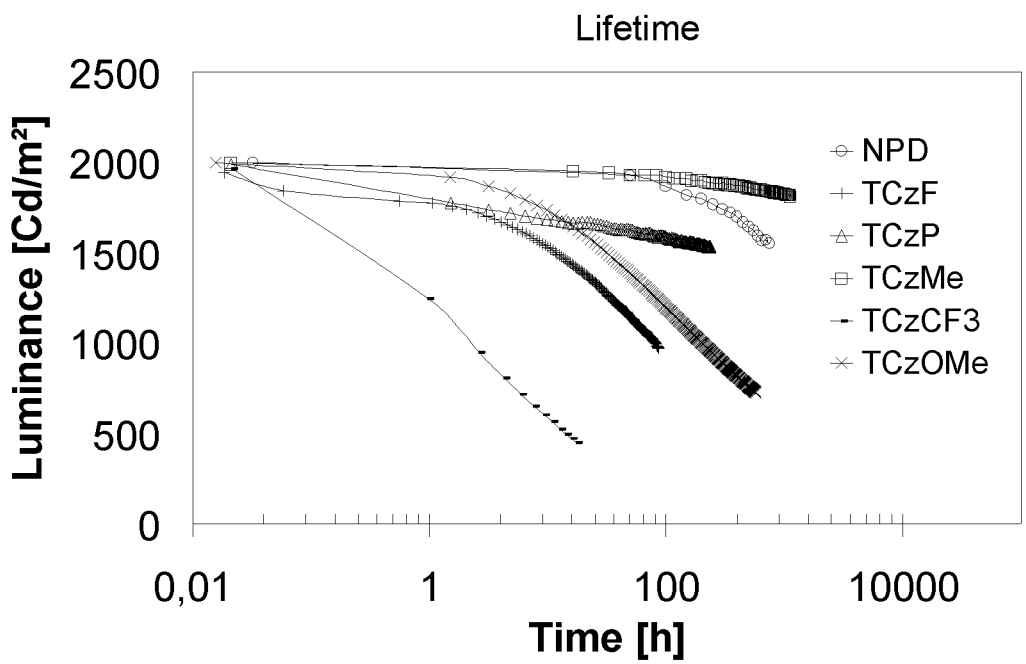
FIG. 1 shows layer configurations in OLED used in the evaluation of N-phenyl triscarbazole derivatives as host in an OLED device made by vacuum process and containing an orange phosphorescent emitter
FIG. 2 shows a luminance-time diagram representing lifetime of OLED comprising N-phenyl triscarbazole derivatives as host.
FIG. 3 shows layer configuration in OLED used in the evaluation of methylphenyl triscarbazole as host in blue OLED.
Figure 4:
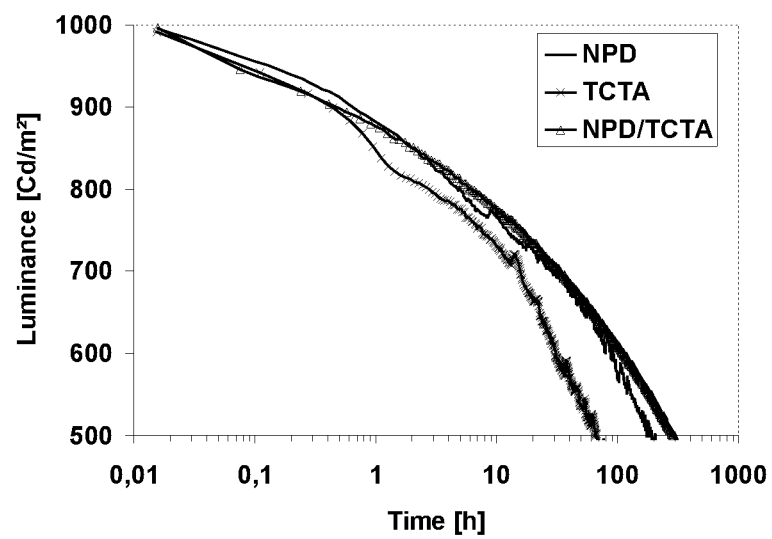
FIG. 4 shows a luminance-time diagram representing lifetime of OLED comprising methylphenyl triscarbazole as host in blue OLED with different HTL.

N-phenyl triscarbazole without any substituent on N-phenyl as shown in the following formula is already described in some prior literatures, such as Japan Patent Application Publication No. JP 2009/021335, International Application No. WO 2009/060757 and WO 2009/060780, and U.S. Patent Application Publication No. US2009/0218938.

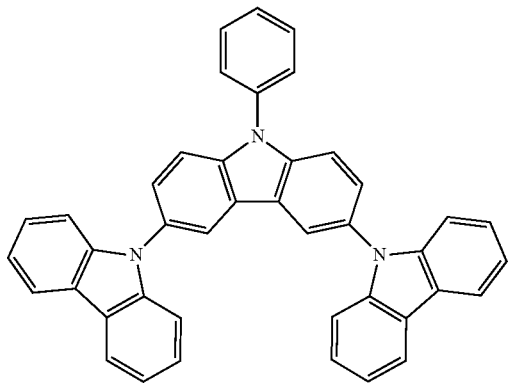 [SMILES: c1ccc(-n2c3ccc(-n4c5ccccc5c5ccccc54)cc3c3cc(-n4c5ccccc5c5ccccc54)ccc32)cc1]

(Unsubstituted) N-phenyl triscarbazole (TCzP)

The present invention provides a host material, which can be represented by Formula (I):

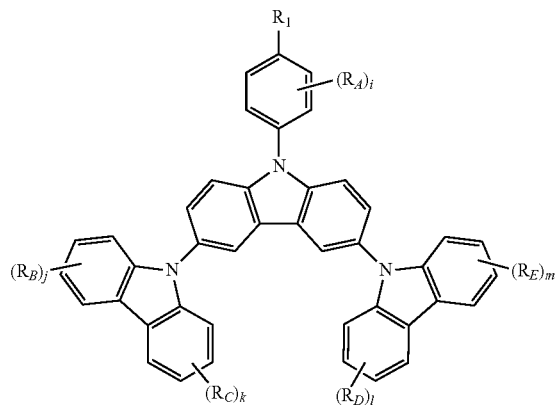

Formula (I)

Wherein:
$R_1$ is selected from the group consisting of:
hydrogen;
halogen; and
alkyl or alkoxy group having 1 to 20 carbon atoms wherein at least one hydrogen atom is optionally replaced by halogen;
$R_A$, $R_B$, $R_C$, $R_D$ and $R_E$ are any of substituents other than hydrogen wherein at least two of $R_1$ and $R_A$ may further form a fused ring,
And
i, j, k, l and m are same or different at each occurrence and represent an integer from 0 to 4, with the proviso that when $R_1$ is hydrogen, i is not 0.

In a preferred embodiment, $R_1$ is one selected from a group consisting of fluorine, methyl, tert-butyl, trifluoromethyl and methoxy. In another embodiment, $R_1$ is alkyl or alkoxy group having 1 to 20 carbon atoms, preferably methyl or t-butyl, more preferably methyl in view of the absence of a heteroatom.

In some embodiments, the other substituents $R_A$, $R_B$, $R_C$, $R_D$ and $R_E$ are any non-heteroatom, preferably hydrogen or linear or branched alkyl chains, more preferably i=0 and $R_B$, $R_C$, $R_D$ and $R_E$ are hydrogen or tert-butyl. In other embodiments, $R_1$ is hydrogen atom and $R_A$ is an aryl group such as phenyl or pyridyl ("pyridine" group). The skilled in the art will appreciate that, as used herein to characterize $R_A$, the term "aryl" should be understood in its broadest meaning, encompassing all those organic radicals derived from an aromatic compound by the removal of one hydrogen atom. The aromatic compound can be any of a large class of compounds that includes benzene and compounds that resemble benzene in certain of their chemical properties. Common aromatic compounds other than benzene include toluene, naphthalene, and anthracene. Each of these compounds contains at least one ring that consists of six carbon atoms, each joined to at least two other carbon atoms, and each joined to adjacent carbon atoms by one single and one double bond. The resulting hexagonal structure is characteristic of many aromatic compounds. The general rule is that aromatic molecules have 4n+2 delocalized electrons (where n is an integral number). Thus the number of delocalized electrons in benzene (6), naphthalene (10), and anthracene (14) agree with their aromatic character. On the other hand, the eight-membered cyclic compound with four alternating double bonds (cyclooctatetraene) is not aromatic and shows reactivity similar to alkenes. For this reason, the bonds in the aromatic ring are less reactive than ordinary double bonds; aromatic compounds tend to undergo ionic substitution (e.g., replacement of a hydrogen bonded to the ring with some other group) rather than addition (which would involve breaking one of the resonant bonds in the ring). Presence of the six-membered benzene ring is not essential for aromatic compounds; for example, furan, a heterocyclic compound that has a five-membered ring that includes an oxygen atom, has aromatic properties, as does pyridine, a heterocyclic compound whose six-membered ring includes a nitrogen atom.

In a specific embodiment, the following compound represented by Formula (II) or (II') is included:

Formula (II)

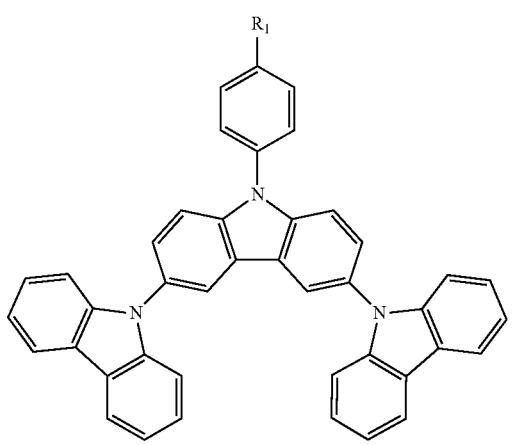

Formula (II')

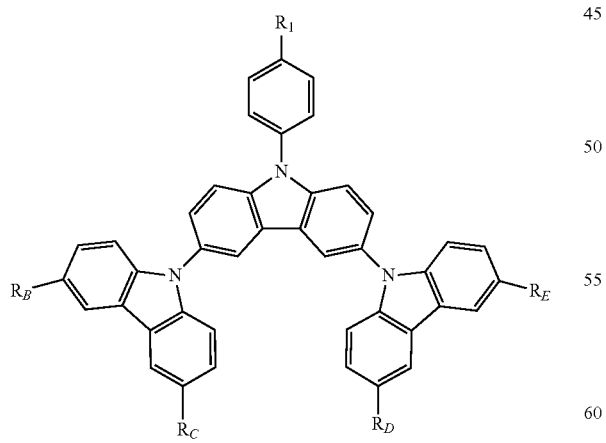

wherein $R_1$, $R_B$, $R_C$, $R_D$, and $R_E$ are the same as defined in Formula (I).

In a more specific embodiment, the following compounds are included.

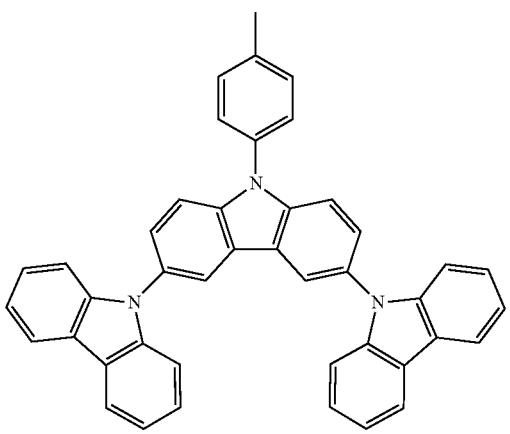

TCzMe

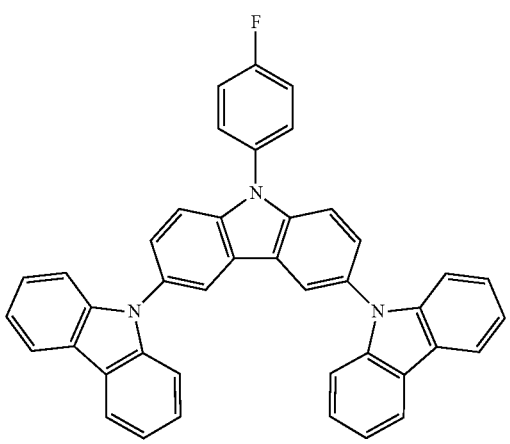

TCzF

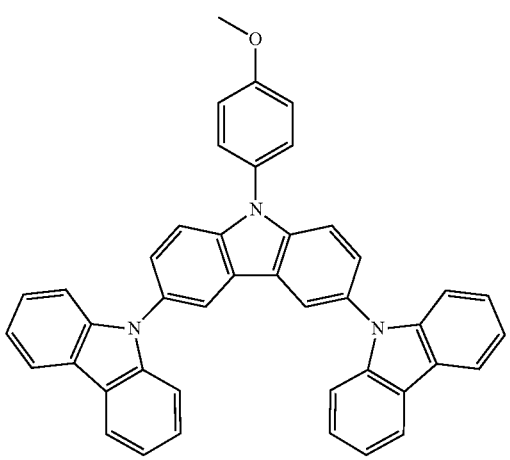

TCzMeO

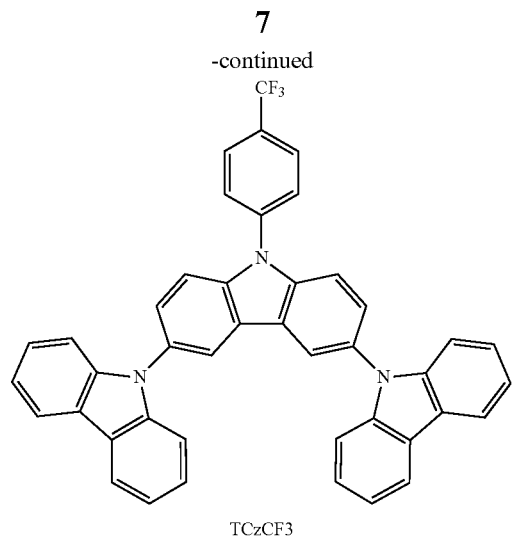

TCzCF3

In other embodiments, the following compounds are included.

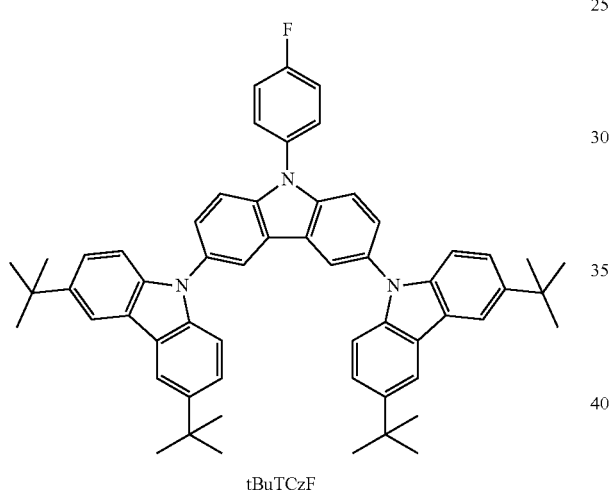

tBuTCzF

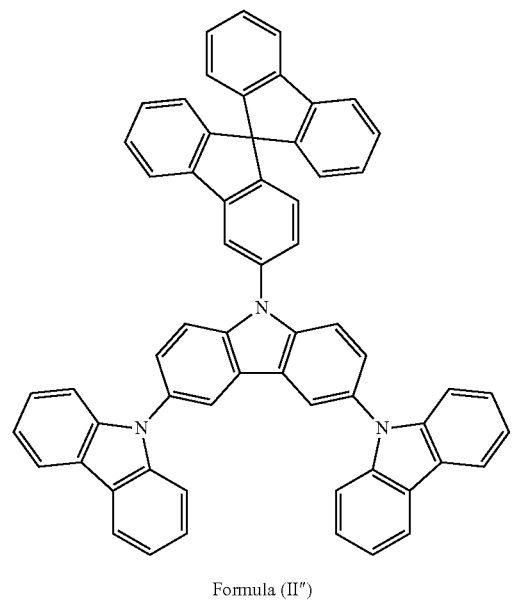

Formula (II″)

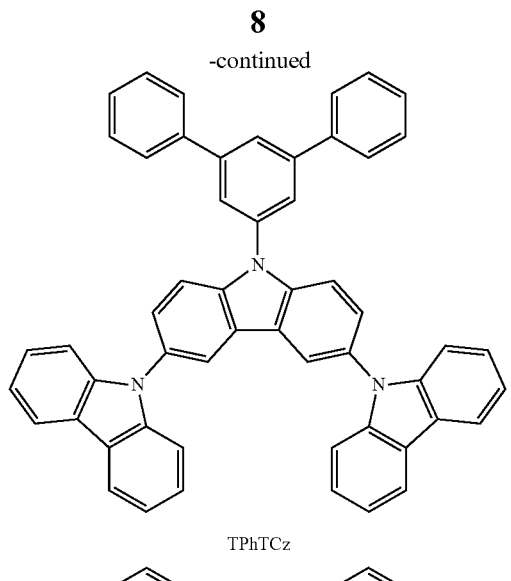

TPhTCz

DPyPhTCz

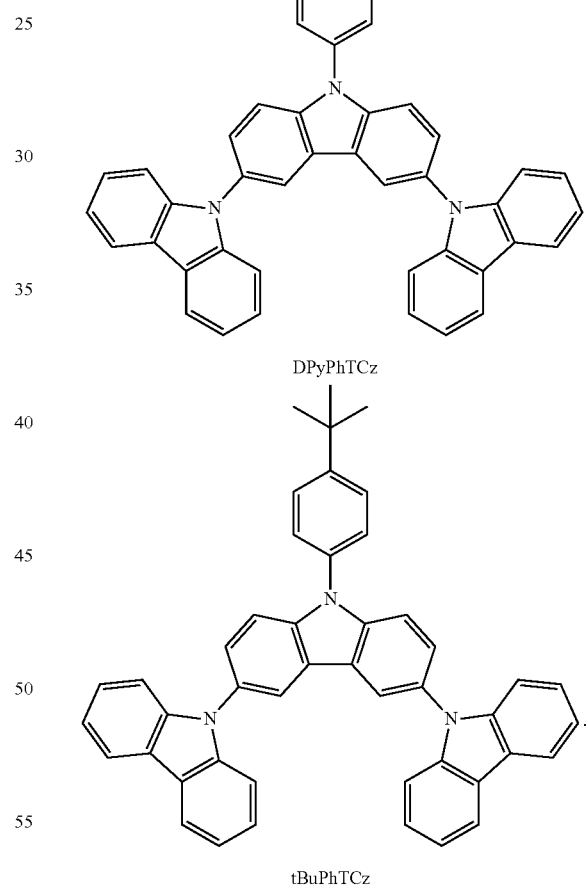

tBuPhTCz

The synthesis of triscarbazole compounds having substituent on N-phenyl of the present invention can be accomplished by any known method. Generally, according to the embodiments of the present invention, the compound of Formula (I) can be prepared by the following reaction scheme, i.e., via an Ullmann coupling reaction of a dihalogenated carbazole compound with the corresponding carbazole derivative.

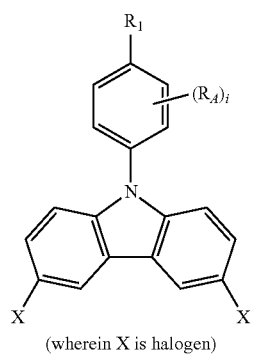

(wherein X is halogen)

+

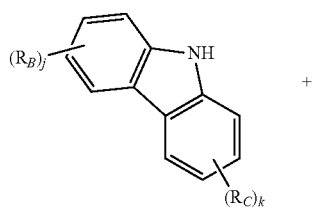

+

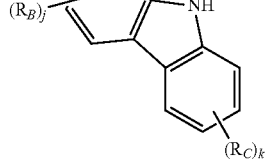

→ Formula (I)

In some embodiments, copper/18-crown-6 is used as a catalyst and potassium carbonate as a base. The details about the Ullmann coupling reaction are described in many references in the art, e.g., Berichte der deutschen chemischen Gesellschaft. 1906, 39(2), 1691-1692.

According to the other embodiments of the present invention, the compound of Formula (I) can be also prepared by reacting triscarbazole (TCzH) with a corresponding halide as follows:

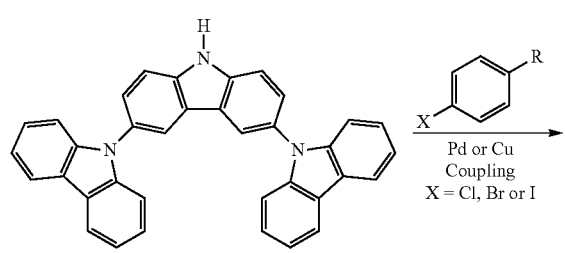

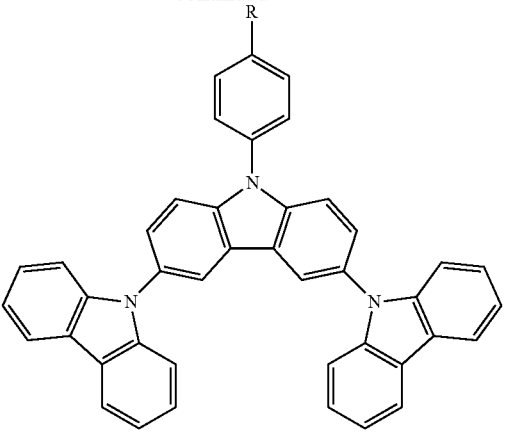

where R is a substituent to the benzene ring.

The triscarbazole compounds having substituent on N-phenyl of the present invention are soluble in organic solvents such as toluene over 1% by weight. Thus, they can be applied to large-scale organic devices since they allow solvent-processing techniques such as spin-coating, (ink-jet) printing processes, high concentration demanding printing processes (roll to roll, flexography, etc), etc., while maintaining the other necessary properties of organic devices.

The present invention is directed to an organic device comprising the N-phenyl triscarbazole compounds of Formula (I) as above and a light emitting compound.

Suitable emitting compounds can be selected from those known in the art and hereafter developed including, without limitation, a metal complex represented by Formula (III):

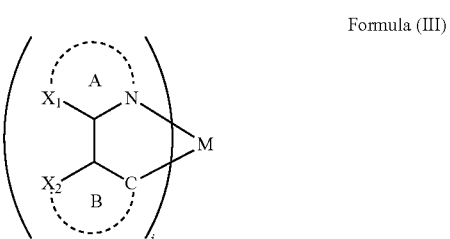

Formula (III)

wherein;

$X_1$ and $X_2$ are same or different at each occurrence and independently selected from the group consisting of C—$R_5$ and N—$R_6$;

wherein $R_5$ or $R_6$ is selected from the group consisting of:

an unshared electron pair;

hydrogen; and other substituents,

A and B are same or different at each occurrence and independently selected from the group consisting of five- or six-membered aryl or heteroaryl rings and fused rings, i represents an integer from 2 to 4 and

M is a metal atom, preferably a platinum-group metal such as Ir, Pt, etc.

In a preferred embodiment, the $X_2$ of Formula (III) is C—H and B is

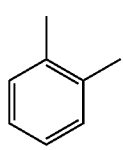

In a more preferred embodiment, the compound of Formula (III) is at least one selected from the following compounds:

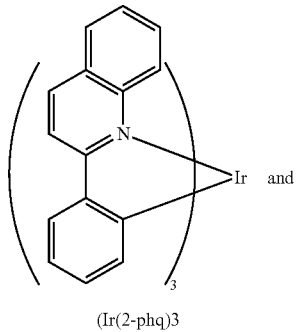

(Ir(2-phq)3)

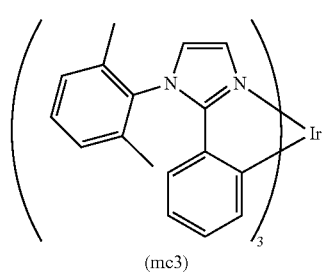

(mc3)

The above mentioned metal complexes, in particular iridium complexes, can exhibit a phosphorescent emission in the visible region of the spectrum. In specific embodiments, the emissive compound exhibits a phosphorescent emission in the blue or green region of the spectrum.

One aspect of the present invention, the above organic device may comprise one layer having both the N-phenyl triscarbazole compound of Formula (I) and a light emitting compound such as a metal complex of Formula (III). Another aspect of the present invention, the above organic device may comprise two layers in which one layer has N-phenyl triscarbazole compound of Formula (I) and the other layer has the light emitting compound.

Also, the above organic device further comprising hole transport layer having a hole-transporting material. Any hole transporting material may be used once it can achieve the purpose of the invention but the preferable materials include 4,4'-bis[N-(1-naphthyl)-N-phenylamino]biphenyl (NPD), 4,4',4''-Tris(N-carbazolyl)triphenyl amine (TCTA), or both thereof, which are in the scope of the present invention.

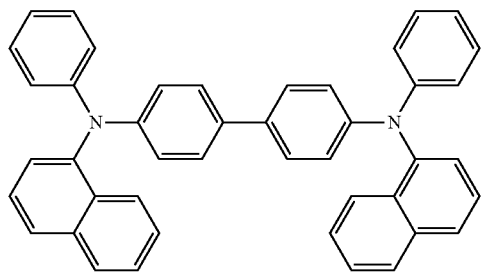

α-NPD

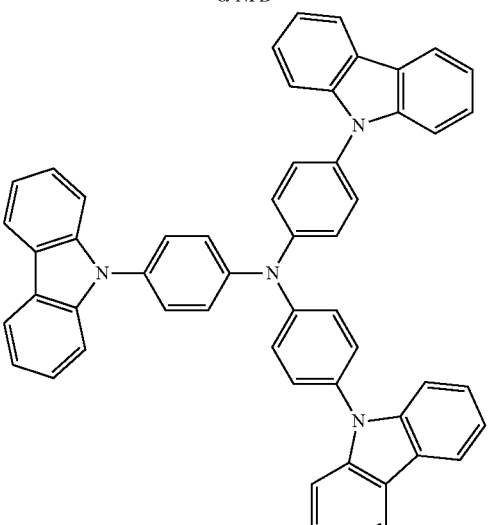

TCTA

Another aspect of the present invention relates to an OLED comprising at least one emitting layer containing N-phenyl triscarbazole compound of Formula (I) and a light emitting compound, specifically the metal complex.

Other aspect of the present invention relates to use of the N-phenyl triscarbazole compound of Formula (I) and a metal complex as defined above in an OLED.

The present invention is also directed to an OLED comprising an emissive layer, wherein the emissive layer comprises the host material described above. The OLED also comprises an emissive material (where the light emitting material is present as a dopant), wherein the emissive material is adapted to emit light when voltage is applied across the device. The emissive material can be a phosphorescent emitter, more specifically an Iridium complex such as those represented by Formula (III) as above.

If the emissive material is used as a dopant in a host layer comprising the N-phenyl triscarbazole compound, then it is generally used in an amount of at least 1 wt %, specifically at least 3 wt %, and more specifically at least 5 wt %, with respect to the total weight of the host and the dopant. Further, it is generally used in an amount of at most 30 wt %, specifically at most 25 wt %.

The OLED generally comprises:
a glass substrate;
a generally transparent anode such as an indium-tin oxide (ITO) anode;
a hole transporting layer (HTL);
an emissive layer (EML);
an electron transporting layer (ETL); and
a generally metallic cathode such as an Al layer.

As for the injection of holes, a hole injection layer (HIL) may be present between the anode and the hole transporting layer. As for the injection of electrons, an electron injection layer (EIL) may be present between the cathode and the electron transporting layer. A hole transporting layer may be present between the HIL and the emissive layer to conduct holes to the emissive layer. An electron blocking layer (EBL) may also be present between the emissive layer and the hole transporting layer. An electron transport layer may be present on the other side of the emissive layer to conduct electrons from the cathode over the electron injection layer to the emissive layer. A hole blocking layer (HBL) may also be present between the emissive layer and the electron transporting layer.

The emissive layer is formed with a host matrix containing the compound described in the present invention wherein the light emitting material is dispersed as a guest. Heavy metal complexes (e.g., Ir complex or Pt complex) may be used a guest for achieving electrophosphorescence. The emissive layer may further comprise an electron-transporting material selected from the group consisting of metal quinoxolates (e.g., aluminium quinolate ($Alq_3$), bis-(2-methyl-8-quinolinolate)-4-(phenylphenolato) aluminium (BAlq), lithium quinolate (Liq)), oxadiazoles (e.g., tetrakis (4-(5-(3,5-di-tert-butylphenyl)-2-oxadiazolyl)phenyl)methane) and triazoles.

The electron transport layer is used to transport electrons into the emissive layer comprising the light emitting material and the host material. The electron transporting material may be an electron-transporting matrix selected from the group consisting of heteroaromatics, metal quinoxolates (e.g., $Alq_3$, BAlq and Liq), oxadiazoles (e.g. 1,3-Bis[5-(4-tert-butylphenyl)-1,3,4-oxadiazole-2-yl]benzene or OXD-7, 2-(4-Biphenylyl)-5-(4-tert-butylphenyl)-1,3,4-oxadiazole or PBD), triazoles (e.g. 3-(4-Biphenylyl)-4-phenyl-5-tert-butylphenyl-1,2,4-triazole or TAZ), substituted phenanthroline (e.g. 2,9-Dimethyl-4,7-diphenyl-1,10-phenanthroline or BCP, 4,7-Diphenyl-1,10-phenanthroline or BPhen), substituted benzimidazoles (e.g. 2,2',2"-(1,3,5-Benzinetriyl)-tris (1-phenyl-1-H-benzimidazole) or TBPI), borane compounds (e.g. tris[3-(3-pyridyl)-mesityl]borane or 3TPYMB) or substituted ketones (e.g. di(9,9'-spirobifluoren-2-yl) ketone or SBFK). A suitable example of the material for the electron transport layer, without limitation, is 4,7-diphenyl-1,10-phenanthroline (Bphen) which has the following formula:

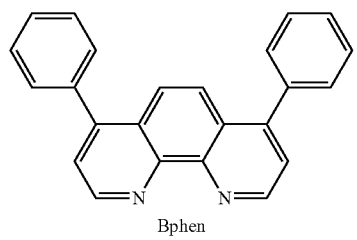 [SMILES: c1ccc(-c2ccnc3c2ccc2c(-c4ccccc4)ccnc23)cc1]

Bphen

The hole transport layer is used to transport holes into the emissive layer comprising the light emitting material and the host material. Suitable examples of the hole transporting material, without limitation, are 4,4'-bis[N-(1-naphthyl)-N-phenylamino]biphenyl(α-NPD) and 4,4',4"-Tris(carbazol-9-yl)triphenylamine (TCTA).

The use of the exciton blocking layer ("barrier layer") to confine excitons within the luminescent layer ("luminescent zone") is advantageous. The exciton blocking layer may be placed between the emissive layer and the electron transport layer as illustrated in FIG. 1. A suitable example of the exciton blocking material is, without limitation, Bis-(2-methyl-8-quinolinolate)-4-(phenylphenolato)aluminium (BAlq):

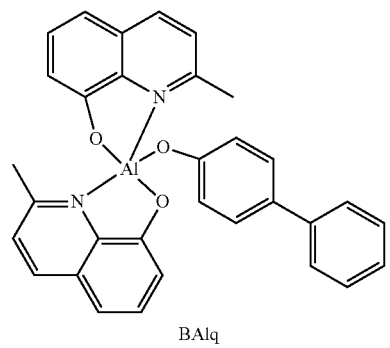

BAlq

The present invention also relates to a use of the compounds according to the present invention in OLED, photovoltaic cells or organic semiconductor devices. It also relates to the use of the compounds of the present invention in a hole transporting layer and/or as a host in an emitting layer

EXAMPLES

Hereinafter, the present invention will be explained in detail with reference to examples and comparative examples. These examples, however, should not in any sense be interpreted as limiting the scope of the present invention. Further, units are expressed by weight unless otherwise described.

Synthetic Methods

Unsubstituted N-phenyl triscarbazole compound (hereafter, TCzP) is prepared as described in prior art references such as JP 2009/021335, WO 2009/060757, WO 2009/060780, and US2009/0218938, which are incorporated hereby as a reference.

Synthetic Example 1

Synthesis of Methyl-Substituted N-Phenyl Triscarbazole Compound

N-(4-tolyl)carbazole—CzMe

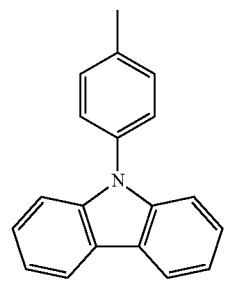 [SMILES: Cc1ccc(-n2c3ccccc3c3ccccc32)cc1]

A mixture of 30.0 g (0.179 mol, 1.0 eq) of carbazole, 50.9 g (0.233 mol, 1.3 eq) of 4-iodo toluene, 173.5 g (1.25 mol, 7.0 eq) of K$_2$CO$_3$, 159.6 g (2.51 mol, 14 eq) of Cu powder and 2.37 g (0.00897 mol, 5 mol %) of 18-crown-6 are stirred in 900 mL of 1,2-dichlorobenzene at 178° C. under N$_2$ atmosphere for 18 h. The reaction is cooled down at room temperature and the mixture is filtered through a path of Celite and silica which is rinsed by toluene. The filtrate is evaporated under vacuum to give a yellow-brown solid further recrystallized from ethanol to give 29.8 g (0.116 mol, 65%) of CzMe as pale yellow needles.

N-(4-tolyl)-3,6-diiodocarbazole—ICzMe

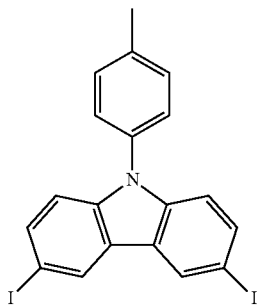 [SMILES: Cc1ccc(-n2c3ccc(I)cc3c3cc(I)ccc32)cc1]

29.00 g (0.113, 1.0 eq) of CzMe are dissolved in 200 mL of refluxing acetic acid. This solution is then cooled down at 100° C. before the subsequent addition of 24.7 g (0.149 mol, 1.12 eq) of KI and 18.8 g (0.0879 mol, 0.78 eq) of KIO$_3$. The reaction is complete after one hour. The white solid is filtered, rinsed by 2×100 ml of 5% Na$_2$S$_2$O$_3$ aqueous solution, 200 mL of water and then dried to give 49.1 g (0.0964 mol, 86%) of ICzMe as a white solid.

N-(4-tolyl)-3,6-bis(carbazol-9-yl)-carbazole—TCzMe

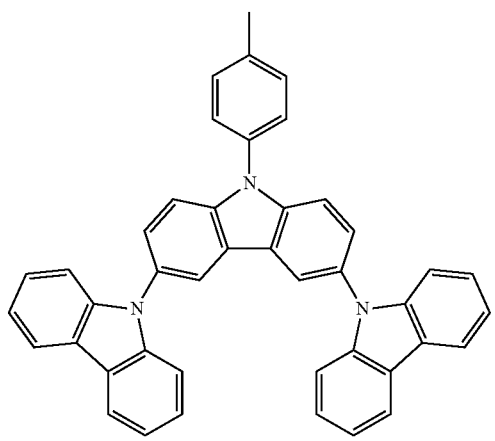 [SMILES: Cc1ccc(-n2c3ccc(-n4c5ccccc5c5ccccc54)cc3c3cc(-n4c5ccccc5c5ccccc54)ccc32)cc1]

49.1 g (0.0964 mol, 1.0 eq) of ICzMe, 37.1 g (0.222 mol, 2.3 eq) of carbazole, 159 g (1.16 mol, 12.0 eq) of K$_2$CO$_3$, 171 g (2.70 mol, 28 eq) of Cu powder and 2.55 g (0.0096 mol, 10 mol %) of 18-crown-6 are stirred in 500 mL of 1,2-dichlorobenzene at 178° C. under N$_2$ atmosphere for 18 h. The reaction is cooled down at room temperature and the mixture is filtered through a path of Celite and silica which is rinsed by toluene. The filtrate is evaporated under vacuum to a give light brown solid further purified by precipitation in CHCl$_3$/EtOH to afford 41.8 g (0.0711 mol, 74%) of TCzMe as a white solid.

Synthetic Example 2

Synthesis of Fluorine Substituted N-Phenyl Triscarbazole Compound

N-(4-fluorophenyl)carbazole—CzF

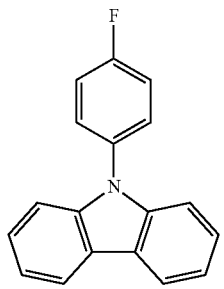 [SMILES: Fc1ccc(-n2c3ccccc3c3ccccc32)cc1]

A mixture of 20 g (0.120 mol, 1.0 eq) of carbazole, 40 g (0.179 mol, 1.5 eq) of 4-iodo-1-fluorobenzene, 116 g (0.837 mol, 7.0 eq) of K$_2$CO$_3$, 106 g (1.67 mol, 14 eq) of Cu powder and 1.58 g (0.006 mol, 5 mol %) of 18-crown-6 are stirred in 500 mL of dry 1,2-dichlorobenzene at 178° C. under N$_2$ atmosphere for 24 h. The reaction is cooled down at room temperature and the mixture is filtered through a path of Celite and silica which is rinsed by toluene. The filtrate is evaporated under vacuum to give a light-brown solid further crystallized from ethanol to give 24.1 g (0.0922 mol, 77%) of CzF.

N-(4-fluorophenyl)-3,6-diiodocarbazole—ICzF

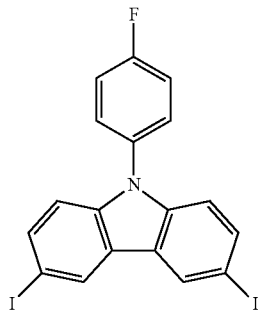 [SMILES: Fc1ccc(-n2c3ccc(I)cc3c3cc(I)ccc32)cc1]

30 g (0.115 mol, 1.0 eq) of CzF are dissolved in 250 mL of refluxing acetic acid. This solution is then cooled down at 100° C. before the subsequent addition of 25.2 g (0.152 mol, 1.32 eq) of KI and 19.2 g (0.0897 mol, 0.78 eq) of KIO$_3$. After one hour, the reaction is done. The white solid is filtered, rinsed by 2×200 ml of 5% Na$_2$S$_2$O$_3$ aqueous solution, 400 mL of water and then dried to give 54.8 g (0.107 mol, 93%) of a white solid

17
N-(4-fluorophenyl)-3,6-bis(carbazol-9-yl-carbazole—TCzF

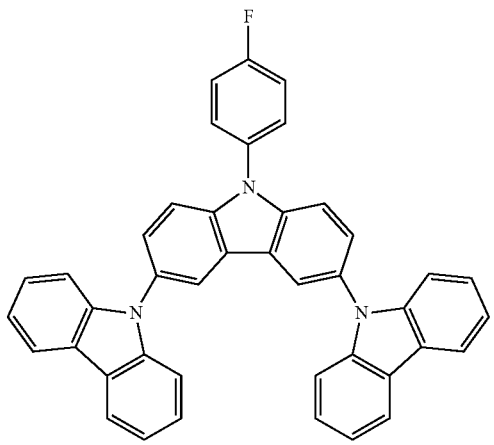 [SMILES: Fc1ccc(-n2c3ccc(-n4c5ccccc5c5ccccc54)cc3c3cc(-n4c5ccccc5c5ccccc54)ccc32)cc1]

30 g (0.0585 mol, 1.0 eq) of ICzF, 22.5 g (0.134 mol, 2.3 eq) of carbazole, 97.0 g (0.702 mol, 12.0 eq) of $K_2CO_3$, 104 g (1.64 mol, 28 eq) of Cu powder and 1.54 g (0.0058 mol, 10 mol %) of 18-crown-6 are stirred in 500 mL of 1,2-dichlorobenzene at 178° C. under $N_2$ atmosphere for 24 h. The reaction is cooled down at room temperature and the mixture is filtered through a path of Celite and silica which is rinsed by toluene. The filtrate is evaporated under vacuum to give a light brown solid further purified by precipitation in $CHCl_3$/EtOH to afford 28.4 g (0.048 mol, 82%) of TCzF as a white solid.

Synthetic Example 3

Synthesis of Methoxy Substituted N-Phenyl Triscarbazole Compound

N-(4-methoxyphenyl)carbazole—CzOMe

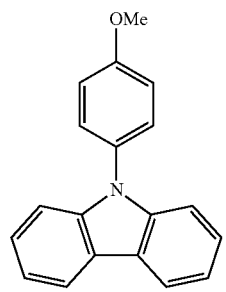 [SMILES: COc1ccc(-n2c3ccccc3c3ccccc32)cc1]

A mixture of 30 g (0.179 mol, 1.0 eq) of carbazole, 54.6 g (0.233 mol, 1.3 eq) of 4-iodoanisole, 173.5 g (1.25 mol, 7.0 eq) of $K_2CO_3$, 160 g (2.51 mol, 14 eq) of Cu powder and 2.37 g (0.00897 mol, 5 mol %) of 18-crown-6 are stirred in 1 L of 1,2-dichlorobenzene at 178° C. under $N_2$ atmosphere for 18 h. The reaction is cooled down at room temperature and the mixture is filtered through a path of Celite and silica which is rinsed by toluene. The filtrate is evaporated under vacuum to give a light-brown solid further crystallized from ethanol to give 28.0 g (0.102 mol, 57%) of CzOMe as white needles.

18
N-(4-methoxyphenyl)-3,6-diiodocarbazole—ICzOMe

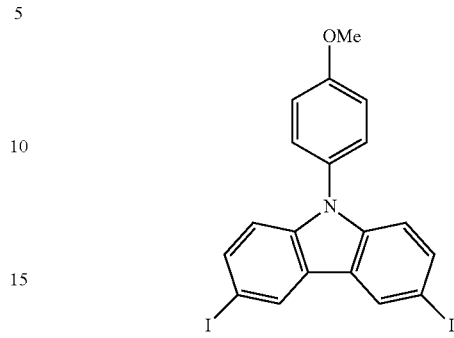

27.5 g (0.101 mol, 1.0 eq) of CzOMe are dissolved in 500 mL of refluxing acetic acid. This solution is then cooled down at 100° C. before the subsequent addition of 22.0 g (0.133 mol, 1.32 eq) of KI and 16.8 g (0.078 mol, 0.78 eq) of $KIO_3$. After two hours, the reaction is done. The white solid is filtered, rinsed by 2×200 ml of 5% $Na_2S_2O_3$ aqueous solution, 400 mL of water and then dried to give 47.9 g (0.0912 mol, 90%) of ICzOMe as a white solid.

N-(4-methoxyphenyl)-3,6-bis(carbazol-9-yl)-carbazole—TCzOMe

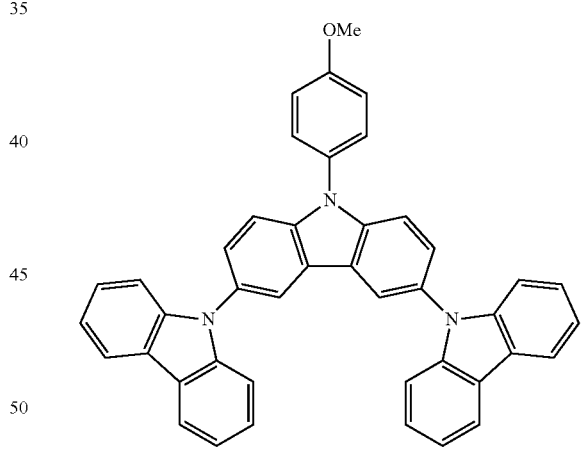

47.8 g (0.0910 mol, 1.0 eq) of ICzOMe, 35.0 g (0.209 mol, 2.3 eq) of carbazole, 150 g (1.09 mol, 12.0 eq) of $K_2CO_3$, 162 g (2.55 mol, 28 eq) of Cu powder and 2.41 g (0.0091 mol, 10 mol %) of 18-crown-6 are stirred in 1 L of 1,2-dichlorobenzene at 178° C. under $N_2$ atmosphere for 18 h. The reaction is cooled down at room temperature and the mixture is filtered through a path of Celite and silica which is rinsed by toluene. The filtrate is evaporated under vacuum to give a light solid further purified by precipitation in $CHCl_3$/EtOH to afford 32.0 g (0.0530 mol, 58%) of TCzOMe as a white solid.

Synthetic Example 4

Synthesis of Trifluoromethyl Substituted N-Phenyl Triscarbazole Compound

N-[4-(trifluoromethyl)phenyl]carbazole—CzCF3

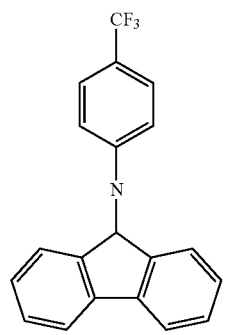 [SMILES: FC(F)(F)c1ccc(NC2c3ccccc3-c3ccccc32)cc1]

A mixture of 15.5 g (0.0926 mol, 1.0 eq) of carbazole, 25.0 g (0.111 mol, 1.2 eq) of 4-(trifluoromethyl)bromobenzene, 26.7 g (0.278 mol, 3.0 eq) of $^t$BuONa, 2.120 g (2.31 mmol, 3 mol %) of Pd$_2$(dba)$_3$ and 5.62 g (0.278 mol, 30 mol %) of tris(tert-butyl) phosphine are stirred in 300 mL of dry toluene at reflux under N$_2$ atmosphere for 16 h. The reaction is cooled down at room temperature and the mixture is filtered through a path of Celite and silica which is rinsed by toluene. The filtrate is evaporated under vacuum to give a light-brown solid further twice recrystallized from ethanol to give 23.4 g (0.075 mol, 81%) of CzCF3 as white solid.

N-[4-(trifluoromethyl)phenyl]-3,6-diiodocarbazole—ICzCF3

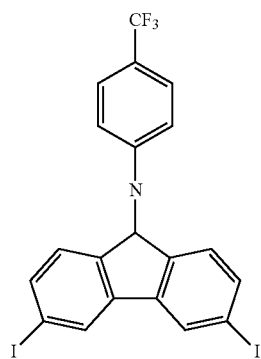 [SMILES: FC(F)(F)c1ccc(NC2c3ccc(I)cc3-c3cc(I)ccc32)cc1]

23.4 g (0.075 mol, 1.0 eq) of CzCF3 are dissolved in 250 mL of refluxing acetic acid. This solution is then cooled down at 100° C. before the subsequent addition of 19.6 g (0.118 mol, 1.57 eq) of KI and 14.9 g (0.070 mol, 0.93 eq) of KIO$_3$. After 1.5 hour, the reaction is complete. The white solid is filtered, rinsed by 2×150 ml of 5% Na$_2$S$_2$O$_3$ aqueous solution, 300 mL of water and then dried to give 30.6 g (0.0544 mol, 72%) of ICzCF as a white solid.

N-[4-(trifluoromethyl)phenyl]-3,6-bis(carbazol-9-yl)-carbazole—TCzCF3

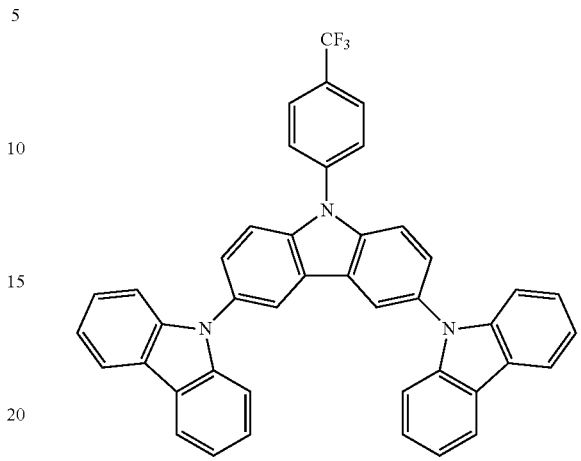

30 g (0.0533 mol, 1.0 eq) of ICzCF3, 20.5 g (0.122 mol, 2.3 eq) of carbazole, 88.3 g (0.640 mol, 12.0 eq) of K$_2$CO$_3$, 94.8 g (1.49 mol, 28 eq) of Cu powder and 1.41 g (0.0053 mol, 10 mol %) of 18-crown-6 are stirred in 500 mL of 1,2-dichlorobenzene at 178° C. under N$_2$ atmosphere for 18 h. The reaction medium is cooled down at room temperature and the mixture is filtered through a path of Celite and silica which is rinsed by toluene. The filtrate is evaporated under vacuum to give a light brown solid further purified by re-precipitation in CHCl$_3$/EtOH to afford 30.8 g (0.0479 mol, 90%) of TCzCF3 as a white solid.

Synthetic Example 5

Synthesis of N-(4-fluorophenyl)-3,6-bis[3,6-tert-butyl-(carbazol-9-yl)]-carbazole 3,6-bis(tert-butyl)carbazole—tBuCz

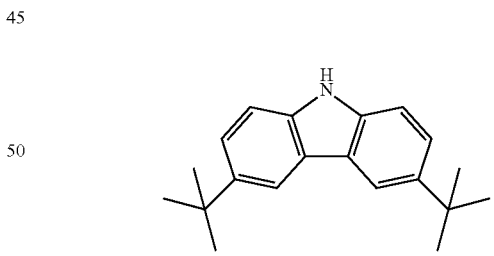

To a suspension of 244 g (1.79 mol, 3.0 eq) of ZnCl$_2$ in a 1 L nitromethane and 100 g (0.598 mol, 1.0 eq) of carbazole solution, 191 g (2.06 mol, 3.4 eq) of tert-butyl chloride are added and the mixture stirred for exactly 5 hours before addition of 1 L of water. The aqueous layer is extracted by 2×500 mL of dichloromethane (DCM) and combined organic layers are then dried over MgSO$_4$ and concentrated. The crude brown sticky oil is then purified by crystallization from ethanol to afford 19.0 g (0.0682 mol, 11%) of white needles.

N-(4-fluorophenyl)-3,6-bis[3,6-tert-butyl-(carbazol-9-yl)]-carbazole—tBuTCzF

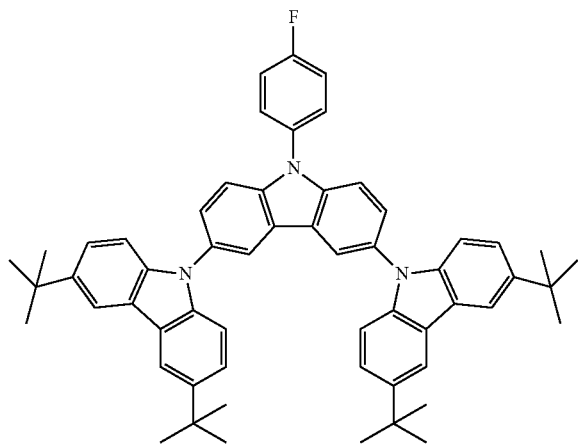 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1ccc(F)cc1]

10.0 g (0.0195 mol, 1.0 eq) of ICzF, 12.5 g (0.0448 mol, 2.3 eq) of tBuCz, 32.3 g (0.234 mol, 12.0 eq) of $K_2CO_3$, 34.7 g (0.546 mol, 28 eq) of Cu powder and 0.515 g (0.0019 mol, 10 mol %) of 18-crown-6 are stirred in 500 mL of 1,2-dichlorobenzene at 178° C. under $N_2$ atmosphere for 18 h. The reaction is cooled down at room temperature and the mixture is filtered through a path of Celite and silica which is rinsed by toluene. The filtrate is evaporated under vacuum to give light brown solid further purified by FC (silica hexanes/DCM) to afford 12.6 g (0.0155 mol, 79%) of tBuTCzF as a white powder.

Synthetic Example 6

Synthesis of N-Tert-Butylphenyl-Triscarbazole

In a one liter flask is introduced $K_3PO_4$ (7 eq) in dioxane, CuI (10% mol), 4-t-butyl-1-iodobenzene (1.25 eq) and tris-carbazole (1 eq) are then added to the medium. After the final addition of 1,2-diaminocyclohexane (0.16 eq) the temperature is raised to 110° C. for 6 h. After cooling, the reaction medium is filtered on a celite pad and washed with THF. The solid recovered by solvent evaporation is flash chromatography (Yield 90%).

Synthetic Example 7

Synthesis of N-Triphenyl-Triscarbazole

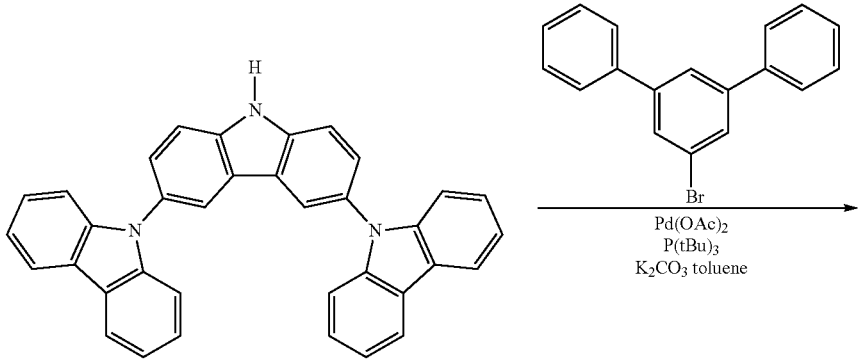

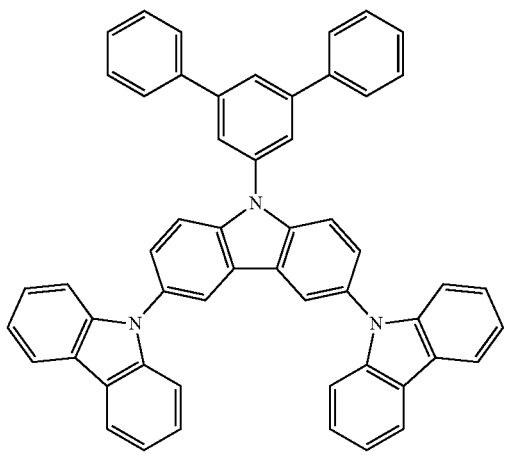

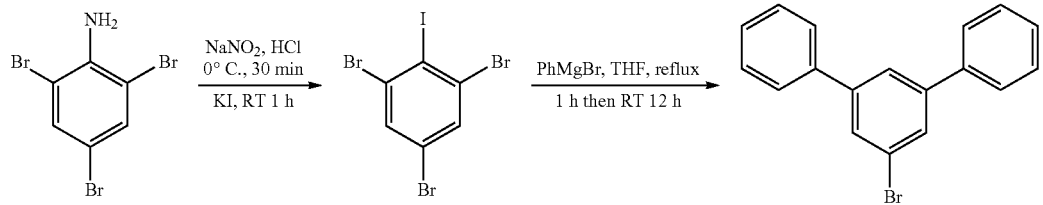

Tribromoiodobenzene as the aryl iodide reagent represented by the formula below was synthesized according to the method disclosed in *Synthesis,* 13, 1979-1983, 2007.

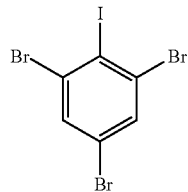

A solution of NaNO$_2$ (1.64 g, 23.8 mmol) in H$_2$O (10 mL) is added dropwise to a mechanically stirred slurry of 2,4,6-tribromoaniline (7.75 g, 23.5 mmol) in concentrated HCl (12 mL) at 0° C. Stirring is continued for 30 min after complete addition of NaNO$_2$. The diazonium salt is slowly transferred to a solution of KI (38.2 g, 0.23 mol) in H$_2$O (60 mL). The solution is stirred vigorously at room temperature for 1 h. CH$_2$Cl$_2$ (100 mL) and 0.5 M Na$_2$SO$_3$ (10 mL) are added successively.

The aqueous layer is separated and washed with CH$_2$Cl$_2$. The combined organic layers are washed with 10% NaOH and saturated NaCl and dried. A red solid is isolated upon solvent removal. Recrystallization (25% hexane—CH$_2$Cl$_2$) affords pure product (5.87 g, 53%).

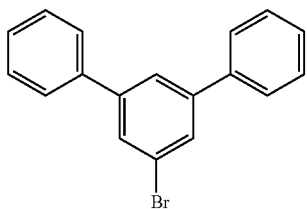 [SMILES: Brc1cc(-c2ccccc2)cc(-c2ccccc2)c1]

A solution of iodotribromoaniline (5.87 g, 13.2 mmol) in anhydrous THF (100 mL) is added dropwise over 1 h to a stirred, refluxing solution of 1 M PhMgBr in THF (135 mL). Reflux is continued for 1 h after complete addition of the iodo-compound. Stirring is continued at room temperature for 12 h. Excess Ph-MgBr is quenched with saturated NH$_4$Cl. The aqueous layer is washed with Et$_2$O. The combined organic layers are washed with saturated NaCl and dried. A white solid is isolated after solvent removal. Recrystallization (40% CH$_2$Cl$_2$—hexane) gives pure product (1.93 g, 47%)

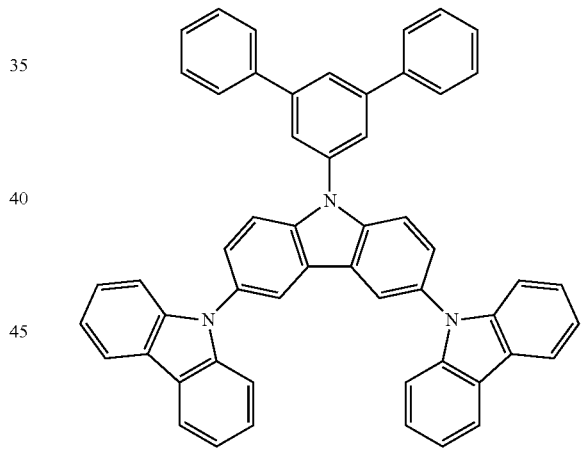

In 400 mL of dry toluene are added 0.02 g of Pd(OAc)$_2$ and 0.25 mL of (tBu)$_3$P. The mixture is deoxygenated with nitrogen for 15 min. The bromo-triphenyl (1.93 g) and the triscarbazole (2.54 g) are then added under nitrogen and stirring. K$_2$CO$_3$ (1.66 g) is added and the reaction temperature is raised to 90° C. After 5 h at 90° C., the reaction mixture is cooled down to room temperature. After work-up and flash chromatography, the target compound is recovered with 53% yield (1.93 g).

Synthetic Example 8
Synthesis of N-3-Spirobifluorene-Triscarbzole
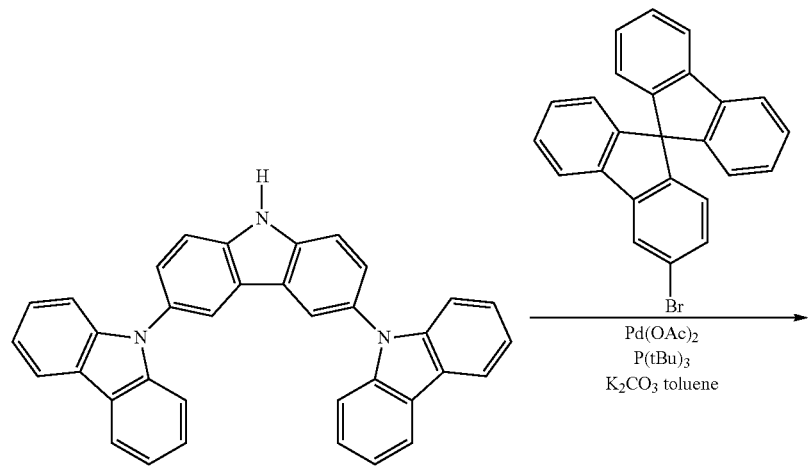
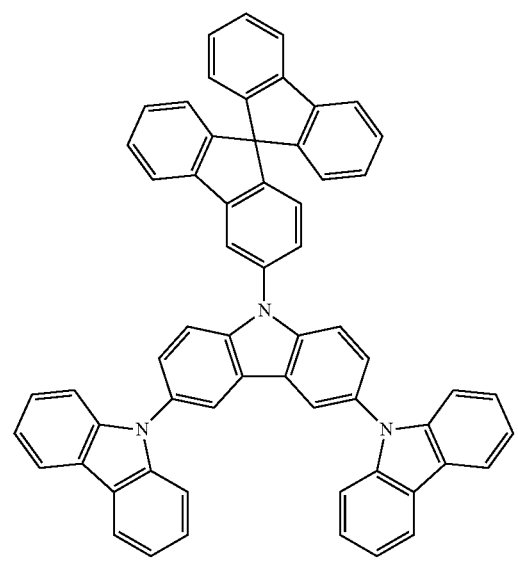

N-3-spirobifluorene-triscarbzole was prepared in the identical manner to Synthetic Example 6 except spirobifluorenylbromide is used instead of bromotriphenyl.

Comparative Example

Synthesis of Non Substituted N-Phenyl Triscarbazole

N-phenyl carbazole—CzP

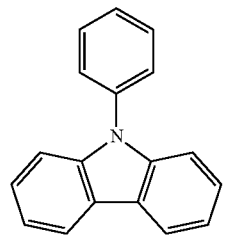 [SMILES: c1ccc(-n2c3ccccc3c3ccccc32)cc1]

A mixture of 30 g (0.179 mol, 1.0 eq) of carbazole, 47.58 g (0.233 mol, 1.3 eq) of iodobenzene, 173.5 g (1.25 mol, 7.0 eq) of K$_2$CO$_3$, 159.6 g (2.51 mol, 14 eq) of Cu powder and 2.371 g (0.00897 mol, 5 mol %) of 18-crown-6 are stirred in 900 mL of 1,2-dichlorobenzene at 178° C. under N$_2$ atmosphere for 18 h. The reaction is cooled down at room temperature and the mixture is filtered through a path of Celite and silica which is rinsed by toluene. The filtrate is evaporated under vacuum to give a yellow-brown solid further recrystallized from ethanol. Collected weight=23.17 g (0.0950 mol, 53%) of CzP as pale yellow needles.

N-phenyl-3,6-diiodocarbazole—ICzP

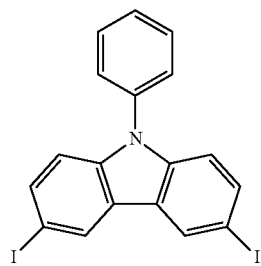 [SMILES: Ic1ccc2c(c1)c1cc(I)ccc1n2-c1ccccc1]

23.17 g (0.0952 mol, 1.0 eq) of CzP are dissolved in 200 mL of refluxing acetic acid. This solution is then cooled down at 100° C. before the subsequent addition of 20.9 g (0.126 mol, 1.32 eq) of KI and 15.9 g (0.074 mol, 0.78 eq) of KIO$_3$. After one hour, the purple iodine disappears what indicates that the reaction is complete. The white solid is filtered, rinsed by 2×100 ml of 5% Na$_2$S$_2$O$_3$ aqueous solution, 200 mL of water and then dried to give 42.9 g (0.0867 mol, 91%) of ICzP as a white solid.

N-phenyl-3,6-bis(carbazol-9-yl)-carbazole—TCzP

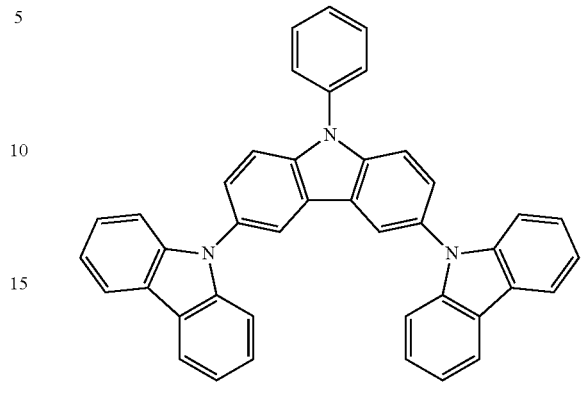

42.9 g (0.0866 mol, 1.0 eq) of ICzP, 33.3 g (0.199 mol, 2.3 eq) of carbazole, 144 g (1.04 mol, 12.0 eq) of K$_2$CO$_3$, 154 g (2.42 mol, 28 eq) of Cu powder and 2.29 g (0.0087 mol, 10 mol %) of 18-crown-6 are stirred in 500 mL of 1,2-dichlorobenzene at 178° C. under N$_2$ atmosphere for 18 h. The reaction is cooled down at room temperature and the mixture is filtered through a path of Celite and silica which is rinsed by toluene. The filtrate is evaporated under vacuum to give a light brown solid further purified by precipitation in CHCl$_3$/EtOH to afford 43.4 g (0.0756 mol, 87%) of TCzP as a white solid.

Characterization of Triscarbazole Compounds of the Present Invention

HOMO-LUMO Measurements

The HOMO and LUMO values are estimated from cyclic voltammetry. The HOMO and LUMO values are respectively obtained from the 1$^{st}$ oxidation potential wave measured in dichloromethane and the 1$^{st}$ reduction potential measured in tetrahydrofuran.

Voltammetric measurements are performed using first a Methrohm VA Tracer Analyser 746 coupled with a computer-controlled AutoLab PGSTAT128N electrochemical workstation coupled with a 663 VA Stand measure unit.

Cyclic voltammograms are recorded under inert atmosphere (argon or nitrogen) in anhydrous dichloromethane or anhydrous tetrahydrofuran using 0.1 M tetrabutylammonium hexafluorophosphate as supporting electrolyte. The working electrode is a glassy carbon disk and the counter electrode a platinum wire. A silver/silver chloride electrode filled with a methanolic saturated KCl solution or a platinum wire pseudo-reference is used as reference electrode. The host solutions (0.5-1 mM) are outgassed with argon before measurement.

Triplet Energy Measurements

The triplet energies of the hosts are calculated from the highest energy peak of the phosphorescence spectra in 2-methyl-THF glasses at 77 K.

Embodiment

Some characteristics of unsubstituted N-phenyl triscarbazole compound (hereafter, TCzP) and N-phenyl triscarbazole compounds having methyl (hereafter, TCzMe), fluorine (hereafter, TCzF), methoxy (hereafter, TCzOMe) or trifluoromethyl (hereafter, TCzCF3) substituent on N-phenyl of the present invention are shown in Table 1. Also included is tBuTCzF, substituted by a fluorine atom on the N-phenyl and 4 tert-butyl moieties on the side carbazoles.

All of these triscarbazoles are soluble in toluene more than 1% by weight. Differences in glass transition temperatures and HOMO and LUMO levels between unsubstituted N-phenyl triscarbazole and substituted N-phenyl triscarbazoles are not significant.

TABLE 1

|  | Tg, °C. | HOMO, eV | LUMO, eV | Triplet E, eV |
|---|---|---|---|---|
| Comparative Example (TCzP) | 146 | −5.51 | −1.61 | 2.95 |
| Example 1 (TCzMe) | 151 | −5.48 | −1.71 |  |
| Example 2 (TCzF) | 152 | −5.52 | −1.77 | 2.95 |
| Example 3 (TCzOMe) | 149 | −5.48 | −1.47 |  |
| Example 4 (TCzCF3) |  | −5.54 | −1.84 |  |
| Example 5 (tBuTCzF) |  | −5.39 | −1.61 |  |

A general structure as shown in FIG. 1 was used to fabricate OLED having an emissive layer (EML) containing above N-phenyl triscarbazole compound and Ir complex.

A reference OLED containing NPD as a host was fabricated to benchmark the performance of the N-phenyl triscarbazole based compounds of the present invention. Keeping the OLED structure identical, devices based on TCzP (comparative example) and TCzMe, TCzF, TCzOMe and TCzCF3 of the invention were fabricated in order to compare device performances with those of device based on NPD. Apart from the compound of the invention, the EML comprises tris(2-phenylquinoline)iridium(III) (Ir(2-phq)$_3$) as a dopant.

Light emitting devices were fabricated as below: a Plexcore OC AQ-1100 supplied from Plextronics was deposited by spin coating on indium tin oxide (ITO) coated glass substrate to a thickness of 60 nm. The obtained film was dried on a hot plate at 200° C. for 10 min. The NPD and the emissive layer (host: Ir(2-phq)$_3$ formulation) were deposited by vacuum deposition to thicknesses of 30 nm and 20 nm, respectively. An 10 nm of barrier layer, namely, Bis-(2-methyl-8-quinolinolate)-4-(phenylphenolato)aluminium (BAlq), was deposited by vacuum deposition onto the EML. An 45 nm of 4,7-diphenyl-1,10-phenanthroline (BPhen):Cs$_2$CO$_3$ layer was co-evaporated onto the barrier layer. Finally, aluminum cathode layer was deposited by thermal evaporation.

Electronic and photometric characterizations were conducted using a Hamamatsu C9920-12 measurement system coupled to a Keithley 2400 source measure unit. All of the device fabrication and characterization steps after spin coating of HIL were carried out in an inert atmosphere.

Table 2 shows efficiencies of devices comprising NPD (as Reference), TCzP (as Comparative Example) and TCzMe, TCzF, TCzOMe and TCzCF3 (as Examples 1 to 4). For the similar operating voltages, work for operation (J) decreased in devices comprising N-phenyl triscarbazole compared to Reference. As such, the luminous efficacy (Lm/W) and brightness (Cd/A) of light increased while the CIE color coordinates (x, y) maintained. This means that the external quantum efficiency of device (EQE) increased in all devices comprising N-phenyl triscarbazole compound as host for Ir complex compared to device comprising NPD as host. The efficiency of device comprising TCzMe is the best among other devices comprising N-phenyl triscarbazole. Particularly, the increasing value in luminescence, brightness, and efficiency of device was almost three times in Example 1 (TCzMe) compared to Reference. The substitution of a phenyl ring of N-phenyl triscarbazole compounds with an appropriate substituent, lead to improved film morphology in a device which may lead to enhanced stability and increased lifetime.

TABLE 2

| Hosts | 1000 cd/m$^2$ | | | | | | |
|---|---|---|---|---|---|---|---|
|  | V | J | EQE* | Lm/W | Cd/A | X | Y |
| NPD (Reference) | 3.1 | 23.8 | 2.2 | 4.3 | 4.2 | 0.59 | 0.41 |
| Comparative Example (TCzP) | 3.2 | 10.8 | 5.6 | 9.0 | 9.3 | 0.60 | 0.40 |
| Example 1 (TCzMe) | 3.0 | 9.0 | 6.2 | 11.5 | 11.2 | 0.59 | 0.40 |
| Example 2 (TCzF) | 3.7 | 13.5 | 4.5 | 6.3 | 7.4 | 0.60 | 0.40 |
| Example 3 (TCzMeO) | 3.0 | 12.6 | 4.7 | 8.3 | 7.9 | 0.60 | 0.40 |
| Example 4 (TCzCF3) | 3.0 | 15.9 | 3.8 | 6.7 | 6.3 | 0.60 | 0.40 |

*external quantum efficiency (%)

FIG. 2 shows lifetimes of above devices. Luminance of above devices was measured over 1000 hours, and device comprising TCzMe shows best performance among others. In FIG. 2, there is an important increase of lifetime with TCzMe, which provides approximately 55 times of lifetime compared to the reference where NPD is used, and exhibited about 5 times of lifetime over TCzP where the phenyl ring is not substituted. Table 3 shows luminance of above devices.

TABLE 3

| Host | L0 | LT50@L0* |
|---|---|---|
| NPD (Reference) | 2000 |  |
| Comparative Example (TCzP) | 2000 | 63000 |
| Example 1 (TCzMe) | 2000 | 265993 |
| Example 2 (TCzF) | 2000 | 87.00 |
| Example 3 (TCzMeO) | 1999 | 201.90 |
| Example 4 (TCzCF3) | 1965 | 2.30 |

*Time at which OLED exhibits 50% of the initial luminescence (unit = hours)

A general structure as shown in FIG. 3 was used to fabricate blue OLED devices having an emissive layer (EML) containing TCzMe of the present invention.

Device fabrication was performed as follows: a Plexcore OC AQ-1100 supplied form Plextronics was deposited by spin coating on indium tin oxide (ITO) coated glass substrates to a thickness of 60 nm. The obtained film was dried on a hot plate at 200° C. for 10 min. The HTL was evaporated on the HIL to a thickness of 30 nm. Emissive layer was obtained by evaporating a TCzMe: mc3 (15 wt % mc3) formulation. Such formulation was deposited on top of the HTL to a thickness of 30 nm. A 5 nm TCzMe was deposited onto the EML. BPhen:CS$_2$CO$_3$ were co-evaporated onto the barrier layer to a thickness of 50 nm. Finally, aluminum cathode layer was deposited by thermal evaporation.

Inventors evaluate the TCzMe of the present invention as host in a blue OLED made by evaporation. Table 4 shows efficiencies of devices comprising different hole transport layers: NPD, 4,4',4''-Tris(N-carbazolyl)triphenyl amine (TCTA) and a bilayer of NPD/TCTA. For the similar operating voltages, work for operation (J) decreased and external quantum efficiency (EQE) and brightness (Cd/A) of devices increased in devices comprising TCTA layer and NPD/TCTA bilayer as hole transport layer compared to those of a device comprising NPD, which means that the efficiencies of devices were improved. Voltage shift after an operating time of 200 hours ($\Delta V_{200h}$) decreased and LT50 (50% lifetime) at 1000 Cd/m$^2$ increased over 200 hours in the device comprising NPD/TCTA bilayer compared to those of a device comprising a NPD or TCTA layer. With these results, it is proved that using the NPD/TCTA bilayer as HTL can bring best performances to an organic device.

TABLE 4

| HTL | V | J | EQE | Lm/W | Cd/A | $\Delta V_{200\,h}$ | LT50 @ 1000 Cd/m$^2$, hours |
|---|---|---|---|---|---|---|---|
| NPD | 5.49 | 5.04 | 7.3 | 11.4 | 19.9 | 0.59 | 191 |
| TCTA | 6.80 | 3.93 | 9.5 | 11.7 | 25.4 | 0.91 | 67 |
| NPD/TCTA | 6.49 | 4.04 | 9.3 | 12.0 | 24.8 | 0.43 | 293 |

It will be apparent to those skilled in the art that various modifications and variations can be made to the present invention without departing from the spirit and scope of the invention. Thus, it is intended that the present disclosure covers the modifications and variations of this invention, provided they come within the scope of the appended claims and their equivalents.

Should the disclosure of any patents, patent applications, and publications which are incorporated herein by reference conflict with the description of the present application to the extent that it may render a term unclear, the present description shall take precedence.

The invention claimed is:
1. A device comprising a compound of Formula (I):

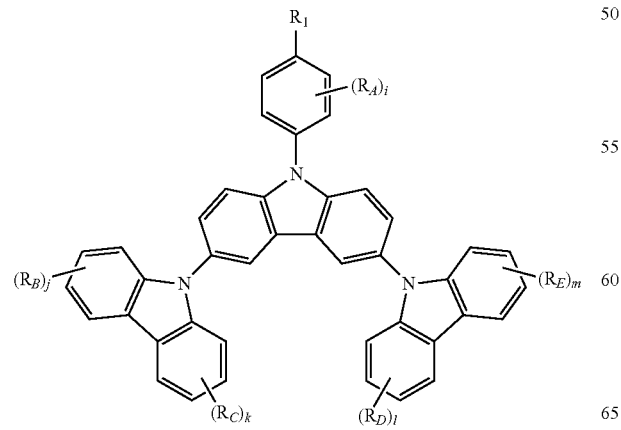

Formula (I)

wherein; $R_1$ is selected from the group consisting of:

halogen; and alkyl group having 1 to 20 carbon atoms wherein at least one hydrogen atom is replaced by halogen;

$R_A$, $R_B$, $R_C$, $R_D$ and $R_E$ are any of substituents other than hydrogen, wherein $R_A$, $R_B$, $R_C$, $R_D$ and $R_E$ are linear or branched alkyl chains, or i of Formula I is 0 and $R_B$, $R_C$, $R_D$ and $R_E$ are alkyl groups; and i, j, k, l, and m of Formula I are same or different at each occurrence and represent an integer from 0 to 4; and a light emitting compound which is at least one selected from the following compounds:

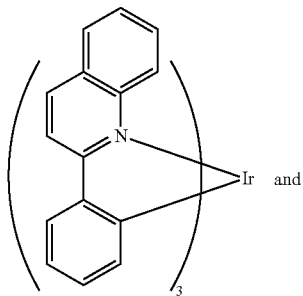 and

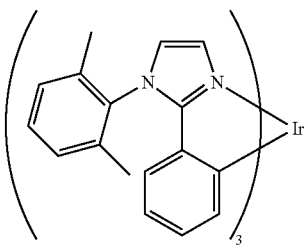

and
wherein the compound of Formula (I) is represented by Formula (II) or (II'):

Formula (II)

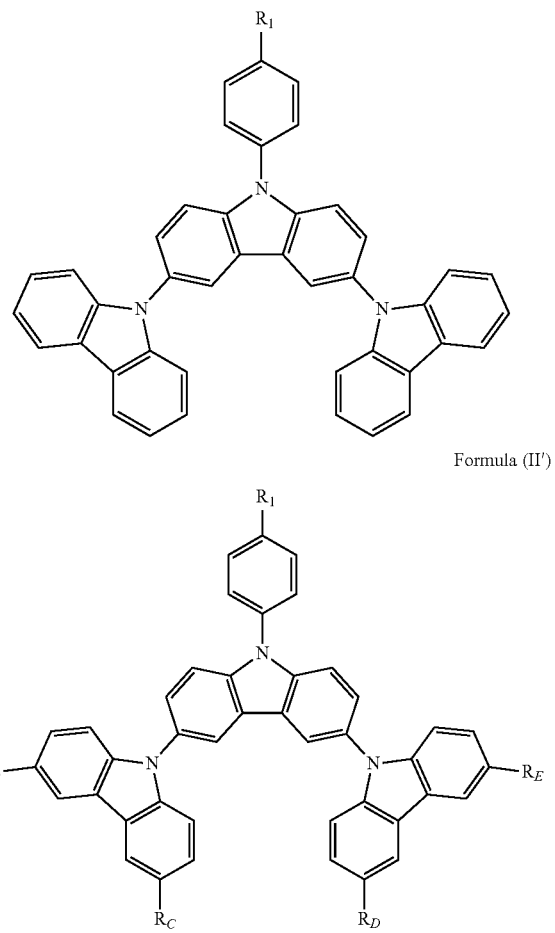

Formula (II')

wherein $R_1$, $R_B$, $R_C$, $R_D$, and $R_E$ are as defined above, and wherein the device is a light emitting device.

2. The device of claim 1, wherein $R_1$ is selected from the group consisting of:
fluorine; and
trifluoromethyl.

3. The device of claim 1, wherein the compound of Formula (I) is represented by Formula (II):

Formula (II)

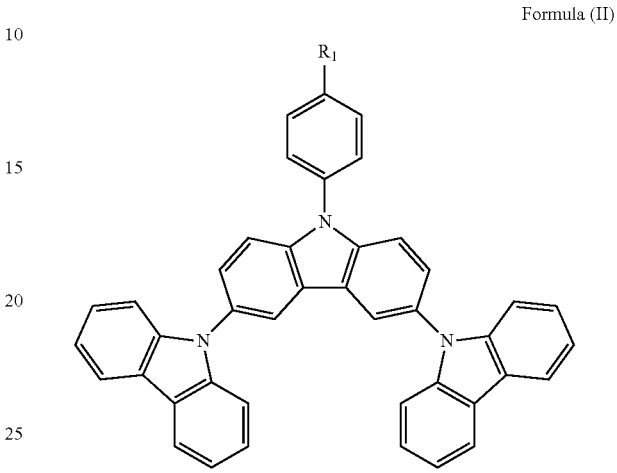

wherein $R_1$ is as defined in claim 1.

4. The device of claim 1, where for Formula I i=0, and $R_B$, $R_C$, $R_D$ and $R_E$ are alkyl groups.

5. The device of claim 1, wherein the device comprises two layers in which one layer has the compound of Formula (I) and the other layer has the light emitting compound.

6. The device of claim 1, wherein the device comprises one layer having both the compound of Formula (I) and the light emitting compound.

7. The device of claim 1, wherein the device is an organic light emitting diode.

8. The device of claim 1 wherein the compounds of formula (I) act as host materials for the light emitting compounds.

* * * * *